United States Patent
Jiang (10) Patent No.: US 10,677,800 B2
(45) Date of Patent: Jun. 9, 2020

(54) BIOMARKERS FOR DIAGNOSIS AND PROGNOSIS OF LUNG CANCER

(71) Applicant: Feng Jiang, Ellicott City, MD (US)

(72) Inventor: Feng Jiang, Ellicott City, MD (US)

(73) Assignees: University of Maryland, Baltimore, Baltimore, MD (US); The United States of America as Represented by the Department of Veterans Affairs, Washington ( * ) Notice: Subject to any disclaimer, the term of this patent is extended or adjusted under 35 U.S.C. 154(b) by 0 days.

(21) Appl. No.: 15/704,828

(22) Filed: Sep. 14, 2017

(65) Prior Publication Data

US 2018/0074059 A1 Mar. 15, 2018

Related U.S. Application Data

(60) Provisional application No. 62/394,533, filed on Sep. 14, 2016.

(51) Int. Cl.
*G01N 33/574* (2006.01)
*C12N 15/113* (2010.01)
*C12Q 1/6886* (2018.01)

(52) U.S. Cl.
CPC ......... *G01N 33/574* (2013.01); *C12N 15/113* (2013.01); *C12Q 1/6886* (2013.01); *C12Q 2600/106* (2013.01); *C12Q 2600/158* (2013.01); *C12Q 2600/178* (2013.01); *G01N 2800/7028* (2013.01)

(58) Field of Classification Search
None
See application file for complete search history.

(56) References Cited

U.S. PATENT DOCUMENTS

2010/0055689 A1* 3/2010 Spira .................... C12Q 1/6886
435/6.14

OTHER PUBLICATIONS

Xing (Clin Cancer Res; 21(2) Jan. 15, 2015).*
Esteller (Nature Reviews Genetic vol. 12 Dec. 2011 pp. 861-874).*
(Krell et al. Frontiers in Bioscience (Elite Edition), vol. 5, pp. 204-213, Jan. 2013; e.g., Abstract).*
McShane et al. British Journal of Cancer, vol. 93, pp. 387-391, 2005).*
Xing (Modern Pathology 2010 vol. 23 pp. 1157-1164).*
Ghorai (Frontiers in Genetics Apr. 2014 vol. 5 article 100).*
Su (Molecular Cancer 2016 15:36 pp. 1-4 Pub online May 12, 2016).*
Su (Oncotarget vol. 7 No. 5 pp. 5131-5142 Pub May 20, 2015).*
Chang (Lung Cancer 71 (2011) pp. 3-10).*

* cited by examiner

*Primary Examiner* — Amanda Haney
(74) *Attorney, Agent, or Firm* — Benjamin Aaron Adler (57) ABSTRACT

Provided herein are methods for non-invasively diagnosing and/or prognosing a lung cancer and for determining the efficacy of a therapeutic treatment regimen for the lung cancer. Expression levels of at least two small non-coding RNAs, for example, microRNAs and small nucleolar RNAs, are measured and used to calculate an area under the curve (AUC) that provides a probability of lung cancer in the subject. The smoking history of the subject and, if present, the size of pulmonary nodules may be incorporated into the calculation.

5 Claims, 6 Drawing Sheets

BIOMARKERS FOR DIAGNOSIS AND PROGNOSIS OF LUNG CANCER

CROSS-REFERENCE TO RELATED APPLICATION

This non-provisional application claims benefit of priority under 35 U.S.C. § 119(e) of provisional U.S. Ser. No. 62/394,533, filed Sep. 14, 2016, the entirety of which is hereby incorporated by reference.

FEDERAL FUNDING LEGEND

This invention was made with government support under Grant Number CA161837 awarded by the National Institutes of Health and Merit Grant Number 101 CX000512 awarded by the U.S. Department of Veterans Affairs. The government has certain rights in the invention.

BACKGROUND OF THE INVENTION

Field of the Invention

The present invention is in the field of lung cancer biology and the diagnosis and prognosis thereof. More specifically, the present invention relates to certain microRNA and small nucleolar RNA biomarkers useful in the early diagnosis and prognosis of lung cancer.

Description of the Related Art

Lung cancer is the number one cancer killer in the USA and worldwide (1). Non-small cell lung cancer (NSCLC) accounts for approximately 85% of all lung cancer cases. Tobacco smoking is the major cause of the disease. The overall 5-year survival rate for stage I NSCLC patients who are typically treated with surgery remains up to 83%. In contrast, only 5-15% and less than 2% of patients with stage III and IV NSCLC are alive after five years (1). These statistics provide the primary rationale to improve NSCLC early detection. Recently, a NCI-National Lung Screening Trail (NLST) showed that the early detection of lung cancer by using low-dose computed tomography (LDCT) significantly reduced the mortality (2). However, 25% of smokers screened by LDCT have indeterminate pulmonary nodules (PNs), of which 95% are determined to be false-positives. Given the high-false positive rate of LDCT, there is large number of referrals for invasive biopsies that carry their own morbidity and mortality, and expensive 2-year multiple follow-up examinations. It is clinically important to develop noninvasive modalities that can accurately identify early stage lung cancer in a safe and cost-effective manner, so that smokers with benign growths can be spared from the biopsies and follow-up examinations, while effective treatments can be immediately initiated for NSCLC (3).

Blood-based biomarkers have been developed for lung cancer early detection and diagnosis. However, blood is a circulating body fluid, molecular changes that can be detected in blood may not specifically associated with lung cancer. Therefore, blood-based biomarkers have a low specificity for lung cancer early detection and diagnosis. In contrast sputum is a noninvasively and easily accessible body fluid that contains exfoliated bronchial epithelial cells (4). Cytological study of sputum can identify morphological abnormalities of bronchial epitheliums, and thus is used for noninvasive diagnosis of lung cancer. However, sputum cytology has a poor sensitivity for detection of lung cancer at the early stage. Molecular study of sputum could detect the molecular abnormalities in the large bronchial airways that reflect those existing in primary lung tumors. Therefore, the analysis of sputum for the molecular changes may provide a noninvasive approach for diagnosis of lung cancer.

Non-coding RNAs (ncRNAs) molecules can regulate a wide range of biological processes, including chromatin remodeling, gene transcription, mRNA translation, and protein function (5). Based on length or number of nucleotides (nts), ncRNAs are divided into three categories (6). First, small ncRNAs are 17-30 nts in length and include microRNAs (miRNAs), piwi-interacting RNAs, and transcription initiation RNAs. Second, middle-size ncRNAs are typically 20 and 200 nts in length and mainly consist of small nucleolar RNAs (snoRNAs). Third, long ncRNAs (lncRNAs) are over 200 nts, which comprise several well-characterized ncRNAs, such as XIST and H19 (7).

It is well documented that dysregulation of miRNAs plays a crucial role in tumorigenesis. Furthermore, new and unexpected functions of middle-size ncRNAs and lncRNAs have been discovered recently, which have highly and actively diverse roles in the processes of carcinogenesis than previously thought (8-15). For example, snoRA42, a middle-size ncRNA, has oncogenic function in the development and progression of NSCLC (10-11). Upregulation of snoRA42 could contribute to lung tumorigenesis by regulating features of tumor-initiating cells (10). Small and middle-size ncRNAs are reproducibly detectable in sputum (16-20).

Therefore, there is a recognized need in the art for the development of the cancer-related non-coding RNAs as potential biomarkers for the detection of malignancies. The prior art is deficient in cancer-related ncRNAs and in methods of using the same for the early diagnosis of and prognosis of cancer. The present invention fulfills this longstanding need and desire in the art.

SUMMARY OF THE INVENTION

The present invention is directed to method for diagnosing a lung cancer in a subject. In the method a first biological sample is obtained from a first subject subject and a second control sample is obtained from a second control subject. Expression levels of at least two small non-coding RNAs (sncRNA) are measured in the first biological sample and in the second control sample. An initial probability of lung cancer in the first subject is calculated from the expression levels of the sncRNAs measured in the first subject and in the second control subject. Lung cancer is diagnosed in the first subject when the initial probability is at least equal to a minimum statistically determined value.

The present invention is directed to a related method for diagnosing a lung cancer comprising a further method step. In the further method step incorporating values representative of the smoking histories and, if present, a size of pulmonary nodules of the first subject and the second control subject are incorporated into the calculating step.

The present invention is directed to another method related to diagnosing a lung cancer comprising further method steps. In the further method steps, in the first subject diagnosed with lung cancer the diagnosing steps described herein are repeated at intervals during and after a treatment regimen for the lung cancer. The area under the curve (AUC) calculated at each interval is compared with the initial AUC. A prognosis for the first subject is determined based on an increase or decrease in the AUC at each interval compared to the initial AUC, wherein an increase over the initial AUC is indicative of a likely poor outcome for the first subject.

The present invention also is directed to a non-invasive method for assessing efficacy of a treatment regimen for a lung cancer in a subject. In the method a treatment is selected for a first subject diagnosed with lung cancer. Expression levels of at least three microRNAs (miR) and at least two small nucleolar RNAs are measured in a sputum sample obtained from the first subject and from a second control subject prior to administering the treatment. A receiver operating characteristic (ROC) curve is generated and an area under the ROC curve (AUC) is calculated where the area under the curve (AUC) comprises a first comparator value. The treatment is administered to the subject and the previous steps are repeated to calculate a second AUC value. The second AUC value is compared to the first comparator value, where a lesser second AUC value indicates that the selected treatment is efficacious against the lung cancer.

The present invention is directed further to a non-invasive method for early detection of a lung cancer in a subject. In the method obtaining a first sputum sample is obtained from a first subject with a history of smoking and a second control sputum sample is obtained from a second control subject. Expression levels of microRNAs miR-21, miR-31, and miR-210 and small nucleolar RNAs snoRD-66 and snoRD-78 are measured in the first sputum sample and in the second control sputum sample. An initial probability of lung cancer in the first subject is calculated from the expression levels of the sncRNAs measured in the first subject and in the second control subject and from values representing smoking-pack-years of the first subject and the second control subject. Lung cancer is diagnosed in the first subject when the initial probability is at least equal to 90%. The present invention is directed a related non-invasive method for the early detection of lung cancer in the subject. In the related method the first subject and the control subject have pulmonary nodules and the calculating step further comprises incorporating the size of the pulmonary nodules in the calculation of the area under the curve.

Other and further aspects, features, and advantages of the present invention will be apparent from the following description of the presently preferred embodiments of the invention given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIGS. 4A-4C is a combined analysis of miRNAs and snoRNAs in sputum illustrating a synergistic effect for lung cancer detection.

DETAILED DESCRIPTION OF THE INVENTION

As used herein, the term "a" or "an", when used in conjunction with the term "comprising" in the claims and/or the specification, may refer to "one", but it is also consistent with the meaning of "one or more", "at least one", and "one or more than one". Some embodiments of the invention may consist of or consist essentially of one or more elements, method steps, and/or methods of the invention. It is contemplated that any method, compound, composition, or device described herein can be implemented with respect to any other device, compound, composition, or method described herein.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "about" refers to a numeric value, including, for example, whole numbers, fractions, and percentages, whether or not explicitly indicated. The term "about" generally refers to a range of numerical values, e.g., +/−5-10% of the recited value, that one of ordinary skill in the art would consider equivalent to the recited value, e.g., having the same function or result. In some instances, the term "about" may include numerical values that are rounded to the nearest significant figure.

As used herein, the term "subject" or "first subject" are interchangeable and refer to any human from which a biological sample or first biological sample, such as a sputum sample, is obtained. Thus, as used herein, the term "control" or "second control subject" are interchangeable and refer to any human from which a control sample or second control sample, such as a sputum sample, is used as a comparator for the purpose of diagnosis, prognosis or other analysis of a lung cancer.

In one embodiment of the present invention there is provided method for diagnosing a lung cancer in a subject, comprising a) obtaining a first biological sample from a first subject; b) obtaining a second control sample from a second control subject; c) measuring expression levels of at least two small non-coding RNAs (sncRNA) in the first biological sample and in the second control sample; d) calculating an initial probability of lung cancer in the first subject from the expression levels of the sncRNAs measured in the first subject and in the second control subject; and e) diagnosing the lung cancer in the first subject when the initial probability is at least equal to a minimum statistically determined value.

Further to this embodiment the method comprises incorporating values representative of the smoking histories and, if present, a size of pulmonary nodules of the first subject and the second control subject into the calculating step. In this further embodiment the values representative of the smoking histories of the first subject and the second control subject may be pack-years of smoking.

In another further embodiment the method comprises in the first subject diagnosed with lung cancer, repeating steps a) to d) at intervals during and after a treatment regimen for the lung cancer; comparing the area under the curve (AUC) calculated at each interval with the initial AUC; and determining a prognosis for the first subject based on an increase or decrease in the AUC at each interval compared to the initial AUC, wherein an increase over the initial AUC is indicative of a likely poor outcome for the first subject. In this further embodiment the increase in the AUC over the initial AUC may be indicative of an aggressive lung cancer.

In all embodiments the the first biological sample and the second control sample each may be a sputum sample. Also in all embodiments the sncRNAs may be microRNAs (miR) or small nucleolar RNAs (snoRNA) or a combination thereof. Particularly, the microRNAs may be miR-21, miR-31, or miR-210 and the small nucleolar RNAs are snoRD-66 or snoRD-78. In addition the first subject may be at risk of having lung cancer. Furthermore, the lung cancer may be small cell lung cancers (SCLC) and non-small cell lung cancers (NSCLC).

In all embodiments measuring the expression levels of the sncRNAs may comprise measuring expression levels of five biomarkers comprising miR-21, miR-31, miR-210, snoRD-66, and snoRD-78. Also calculating the probability of lung cancer may comprise generating a receiver operating characteristic (ROC) curve; and calculating an area under the ROC curve (AUC), where the area under the curve (AUC) provides the probability of lung cancer in the first subject. In addition the minimum statistically determined value of the probability is at least 80%. Particularly, the minimum statistically determined value of the probability is at least 90%.

In another embodiment of the present invention there is provided a non-invasive method for assessing efficacy of a treatment regimen for a lung cancer in a subject, comprising a) selecting a treatment for a first subject diagnosed with lung cancer; b) measuring expression levels of at least three microRNAs (miR) and at least two small nucleolar RNAs in a sputum sample obtained from the first subject and from a second control subject prior to administering the treatment; c) generating a receiver operating characteristic (ROC) curve; d) calculating an area under the ROC curve (AUC), said area under the curve (AUC) comprising a first comparator value; e) administering the treatment to the subject; f) repeating steps b) to d) to calculate a second AUC value; g) comparing the second AUC value to the first comparator value; where a lesser second AUC value indicates that the selected treatment is efficacious against the lung cancer.

In this embodiment the microRNAs may be miR-21, miR-31, and miR-210 and the small nucleolar RNAs may be snoRD-66 and snoRD-78. Also in this embodiment the lung cancer may be small cell lung cancers (SCLC) and non-small cell lung cancers (NSCLC).

In yet another embodiment of the present invention, there is provided a non-invasive method for early detection of a lung cancer in a subject, comprising a) obtaining a first sputum sample from a first subject with a history of smoking; b) obtaining a second control sputum sample from a second control subject; c) measuring expression levels of microRNAs miR-21, miR-31, and miR-210 and small nucleolar RNAs snoRD-66 and snoRD-78 in the first sputum sample and in the second control sputum sample; d) calculating an initial probability of lung cancer in the first subject from the expression levels of the sncRNAs measured in the first subject and in the second control subject and from values representing smoking-pack-years of the first subject and the second control subject; and e) diagnosing the lung cancer in the first subject when the initial probability is at least equal to 90%. Further to this embodiment, the first subject and the control subject may have pulmonary nodules and the calculating step d) comprises incorporating the size of the pulmonary nodules in the calculation of the area under the curve. In both embodiments the lung cancer may be non-small cell lung cancer.

Provided herein are small non-coding RNAs (ncRNA) which when analyzed for changes in or dysregulation of expression levels in combination compared to controls are useful as biomarkers in methods of diagnosing and/or prognosing a non-small cell lung cancer (NSCLC) or a small cell lung cancer (SCLC), preferably a non-small cell lung cancer. An advantage with these methods is that they are non-invasive and demonstrate an improvement in early detection over traditional methods such as low-dose computer tomography (LDCT) or sputum cytology alone. Only a sputum sample is required from a subject of interest to assay for expression levels of the ncRNAs although other biological fluids, such as urine, are contemplated.

The non-coding RNAs used herein as biomarkers in diagnostic and/or prognostic assays are microRNAs (miR-NAs) and small nucleolar RNAs. Particularly a combination of miRNAs and/or snoRNAs are utilized. In a non-limiting example, the sputum miRNA biomarkers are miR-21, miR-31 and miR-210. As a panel, these miR biomarkers exhibit 82.61% sensitivity and 85.45% specificity in detecting a lung cancer, for example NSCLC. Also, in a non-limiting example, the sputum snoRNA biomarkers are snoRD-66 and snoRD-78 which, as a panel, exhibit 73.91% sensitivity and 83.64% specificity for detecting lung cancer. As a first demonstration, a panel comprising these five sputum biomarkers synergistically exhibit 89.13% sensitivity and 89.09% specificity for detecting lung cancer. Thus, the present invention contemplates the inclusion of additional ncRNAs with the five biomarkers provided herein that increase the sensitivity, specificity and accuracy of detection over that exhibited by the panel of miR-21, miR-31, miR-210, snoRD-66 and snoRD-78. For example, Table 3 lists additional miRNAs whose expression in sputum is associated with lung cancer, for example, NSCLC.

A subject of interest or first subject may be, but not limited to, a lung cancer patient, an undiagnosed smoker or other undiagnosed subject presenting with one or more symptoms associated with lung cancer or having pulmonary nodules not yet diagnosed as malignant. A second control subject may be a healthy subject, either smoker or non-smoker, a subject who has been free of lung cancer for at least two years, or a subject with benign pulmonary nodules, either smoker or non-smoker.

Thus, the present invention provides a method for diagnosing a lung cancer in a subject. The sputum biomarkers are useful in establishing a specific diagnosis via determining and quantifying expression levels of the biomarker panel or combination thereof. This is particularly important when there is a need to determine whether lung tumors are of primary or metastatic origin.

Moreover, the sputum biomarkers enable early detection. The sputum biomarkers function as an easy-to-perform assay for expression levels at a first screening to pre-identify smokers for lung cancer. Subsequently screening the pre-identified individuals using CT imaging is costly way to diagnose lung cancer. Using the sputum biomarkers for specifically identifying lung cancer in a CT screening positive setting reduces the lung cancer-related mortality by i), sparing smokers with benign PNs from the invasive biopsies and expensive follow-up examinations, ii) improving CT for precisely and preoperatively identifying lung cancer, and iii) facilitating effective treatments to be instantly initiated for lung cancer. As such, the sputum biomarkers are useful for risk assessment. The sputum biomarkers enable a quantitative, probabilistic method to determine when heavy smokers are predisposed to lung cancer.

The present invention provides a method for determining a prognosis of a lung cancer patient. The composite panel of sputum biomarkers is quantified in a sputum sample obtained after a subject is diagnosed with lung cancer. Periodic analysis of the sputum biomarkers in the subject is useful in determining the aggressiveness of an identified cancer as well as its likelihood of responding to a given treatment.

As such, also provided are methods of determining a treatment regimen for a subject diagnosed with a lung cancer. One of ordinary skill in the art is well able to assess the subject diagnosed with a lung cancer taking into consideration, for example, but not limited to, the age, sex and health considerations other than the cancer, the cancer stage, current medications, etc. to determine which chemotherapeutic or other therapeutic drugs and/or interventions to use. Moreover, once effected the response to the determined treatment regimen can be monitored over time via periodic assays of sputum samples obtained from the subject. A comparison of the expression level of the sputum biomarkers over time is an indicator of therapeutic effectiveness.

The following example(s) are given for the purpose of illustrating various embodiments of the invention and are not meant to limit the present invention in any fashion.

EXAMPLE 1

Methods and Materials
Patient Cohorts

The protocol was approved by the Institutional Review Boards of the Baltimore VA Medical Center and the University of Maryland Medical Center. Consent was obtained from lung cancer patients and control subjects in the Medical Centers. Final diagnoses for lung cancer were confirmed by using histopathologic examinations of biopsy and surgical tissue specimens. Computer tomography (CT) imaging was performed using a standard clinical protocol. Two board-certified radiologists independently read the CT imaging. A positive result from the CT image was determined according to the Fleischner Society-guidelines for management of small pulmonary nodules detected on CT scans (21-23). The surgical pathologic staging was determined according to the TNM classification of the International Union Against Cancer with the American Joint Committee on Cancer and the International Staging System for Lung Cancer. Histopathologic classification was determined according to the World Health Organization classification.

Control individuals were 55-74 years old and heavy smokers and had no prior history of any cancer. All control subjects remained cancer free for a minimum 2-year follow-up. The demographic and clinical characteristics of the recruited subjects, such as stage and histological diagnosis, smoking history, size of pulmonary nodules (PN), and pulmonary functions represented by forced expiratory volume in 1 second (FEV1)/forced vital capacity (FVC) also were collected.

Sample Collection, Preparation, and Sputum Cytology

Before receiving any treatment, the participants were asked to spontaneously cough sputum as previously described (16, 18, 20, 24-36). The participants who could not spontaneously cough sputum were asked to use a Lung Flute (Medical Acoustics, Buffalo, N.Y.)-based technique for sputum induction (28). Sputum was centrifuged at 1,000×g for 15 min. Cytospin slides were prepared from sputum samples for assessing if the samples were representative of deep bronchial cells and cytological study (4). Positive sputum cytology comprised carcinoma in situ and invasive carcinoma (4). Cell pellets from each sample were stored at −80° C. until being tested for the following molecular analysis.

Analyzing Expressions of the ncRNAs in Sputum by Using Quantitative Reverse Transcriptase PCR (qRT-PCR)

Figure 1:
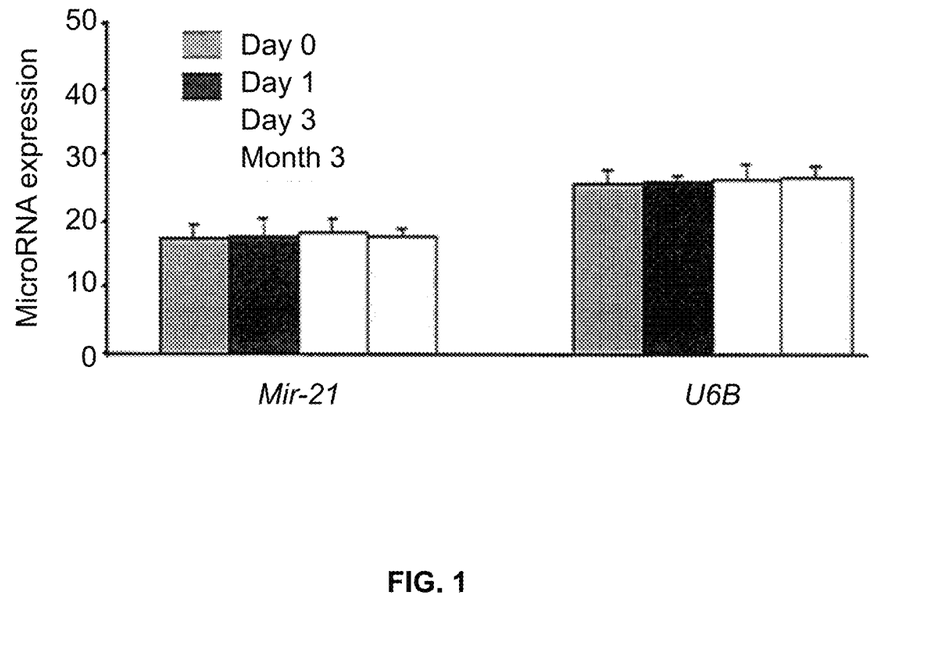
FIG. 1 illustrates expression of miR-21 and U6B over time demonstrating stability in sputum.

Small ncRNAs are highly stable in sputum due to small size and resistance to nucleases (FIG. 1) RNA was extracted from sputum using a previously established protocol (16, 18, 20, 27, 28, 30). The purity and concentration of RNA was determined by using OD260/280 readings with a dual beam UV spectrophotometer (Eppendorf AG, Hamburg, Germany). RNA integrity was determined by using capillary electrophoresis with the RNA 6000 Nano Lab-on-a-Chip kit and the Bioanalyzer 2100 (Agilent Technologies, Santa Clara, Calif.). Expression of the five ncRNAs (miRs-21, 31, and 210, and snoRDs-66 and 78) was determined by using qRT-PCR with Taqman miRNA assays (Applied Biosystems, Foster City, Calif.) as previously described (16, 18, 20, 27, 28, 30). Expression levels of the genes were calculated by using the comparative cycle threshold (Ct) method (16, 18-20, 30). Ct values of the target noRNAs were normalized in relation to that of U6, and determined relative expression of a ncRNA in a given sample using the equation $2-\Delta Ct$, where $\Delta Ct=Ct$ (targeted ncRNA)−Ct (U6) (17, 19-20). Two interplate controls and one no-template control were carried along in each experiment. All experiments were performed at least three times. Five small non-coding RNAs, mir-21, mir-31, mir-210, snoRD66, and snoRD78 are upregulated.

Statistical Analysis

A receiver operating characteristic (ROC) curve and the area under the ROC curve (AUC) were used to determine sample size. The AUC of H0 (the null hypothesis) was set at 0.5. H1 represented the alternative hypothesis; accordingly, at least 28 individuals were required in each category to show a minimum difference of interest between an AUC of 0.75 versus an AUC of 0.5 with 80% power at the 5% significance level. Furthermore, a final clinical-pathologic diagnoses was used as the gold standard to determine the performance of each gene in the detection of lung cancer. A Wilcoxon rank-sum test was used to determine gene expression difference between case and control groups, and to compute Spearman rank correlations among the expressions and with clinical-pathologic variables. Also a Pearson's correlation analysis was used to assess the association between the genes' expressions and demographic and clinical characteristics of the cancer cases or cancer-free controls. An ROC curve and the AUC was applied to evaluate sensitivity, specificity, accuracy, and corresponding cut-off value of each ncRNA. Logistic regression (20) was applied to identify composite panels of biomarkers that could distinguish NSCLC patients from control subjects.

EXAMPLE 2

Analysis of Genes in Sputum from Lung Cancer Patients

Sputum was obtained from 92 lung cancer patients and 81 smokers with benign pulmonary nodules. Demographic and clinical information is shown in Table 1.

TABLE 1

Demographic and clinical information of cancer patients

| Variable | | Cancer | Benign | p-value |
|---|---|---|---|---|
| Age (year) | 25-83 | 41-81 | 25-83 | <0.0001 |
| Mean | 60.18 | 63.95 | 55.91 | |
| SD | 12.04 | 8.96 | 13.6s | |
| Race | | | | 0.2715 |
| White | 83 | 48 | 35 | |
| AA | 89 | 44 | 45 | |
| Native Indian | 1 | 0 | 1 | |
| Gender | | | | 0.5116 |
| Male | 130 | 71 | 59 | |
| Female | 43 | 21 | 22 | |
| Smoking package/year | 0-250 | 0-250 | 0-75 | <0.0001 |
| Mean | 35.65 | 51.38 | 17.79 | |
| SD | 36.60 | 39.20 | 22.91 | |
| CT diagnosis | | | | <0.0001 |
| Cancer | 69 | 63 | 6 | |
| Non-cancer | 104 | 29 | 75 | |
| Final diagnosis | | | | |
| SCLC | 18 | | | |
| NSCLC | 70 | | | |
| other | 4 | | | |
| Stage | | | | |
| I | 1 | | | |
| Ib = 1.5 | 3 | | | |
| II = 2 | 3 | | | |
| IIb = 2.5 | 2 | | | |
| IIIa = 3 | 9 | | | |
| IIIb = 3.5 | 14 | | | |
| IV = 4 | 29 | | | |
| missing | 31 | | | |

49 genes were found in the sputum samples and analyzed for changes. Changes in 23 genes are associated with lung cancer (Table 2).

TABLE 2

Genes in sputum associated with lung cancer

| Gene | Pearson's Coefficient | p-value | Estimated AUC |
|---|---|---|---|
| M16-7a | 0.208 | 0.0100 | 0.623 |
| M16-31 | 0.167 | 0.0357 | 0.605 |
| M16-126 | 0.478 | <0.0001 | 0.775 |
| M16-486 | 0.486 | <0.0001 | 0.786 |
| M16-652 | 0.177 | 0.0423 | 0615 |
| sno61-mi16 | 0.349 | <0.0001 | 0.698 |
| sno66-mi16 | 0.410 | <0.0001 | 0.762 |
| sno76-mi16 | 0.339 | <0.0001 | 0.766 |
| sno78-mi16 | 0.337 | <0.0001 | 0.708 |
| sno116-mi16 | 0.366 | <0.0001 | 0720 |
| snoR33-mi16 | 0.288 | 0.0001 | 0.699 |
| snoR3-mi16 | 0.283 | 0.0002 | 0.684 |
| snoR42-mi16 | 0.350 | <0.0001 | 0717 |
| U6-7a | 0.321 | <0.0001 | 0.674 |
| U6-31 | 0.329 | <0.0001 | 0.679 |
| U6-34a | 0.311 | 0.0002 | 0.675 |
| U6-126 | 0.477 | <0.0001 | 0.765 |
| U6-146 | 0.207 | 0.0094 | 0.610 |
| U6-205 | 0.204 | 0.0083 | 0.619 |
| U6-210 | 0.219 | 0.0045 | 0.609 |
| U6-375 | 0.238 | 0.0019 | 0.638 |
| U6-486 | 0.507 | <0.0001 | 0.773 |
| U6-652 | 0.349 | <0.0001 | 0.692 |

Since the expressions of genes are significantly correlated, logistic regression models with constrained parameters as in least absolute shrinkage and selection operator (LASSO) based on ROC Criterion to eliminate the large number of irrelevant signatures. From the 23 genes, two sputum genes U6-486 and M16-126 are selected as biomarkers for lung cancer (p=0.0007 and 0.0003). The logistic model is $Pr(y=1,cancer|U_1)=\exp(U_1)/1+\exp(U_1)$, and $U_1=-0.302+0.175\times\log_2(U6-486)+0.336\times\log_2(M16-126)$.

Figure 2A:
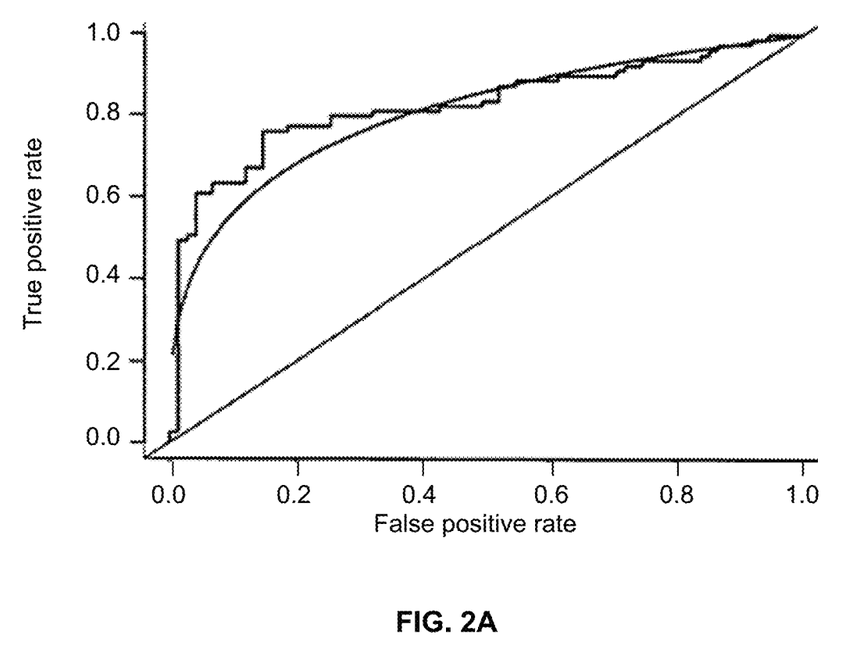
FIGS. 2A-2B are AUC curve plots based on U6-486 and M16-126 (FIG. 2A) and U6-486 and M16-126 with CT (FIG. 2B)

The estimated AUC is 0.828. With the cut-off point Pr(y=1)=0.590, the sensitivity and specificity of using the two genes or biomarkers are 0.760 and 0.853, respectively (FIG. 2A).

Figure 2B:
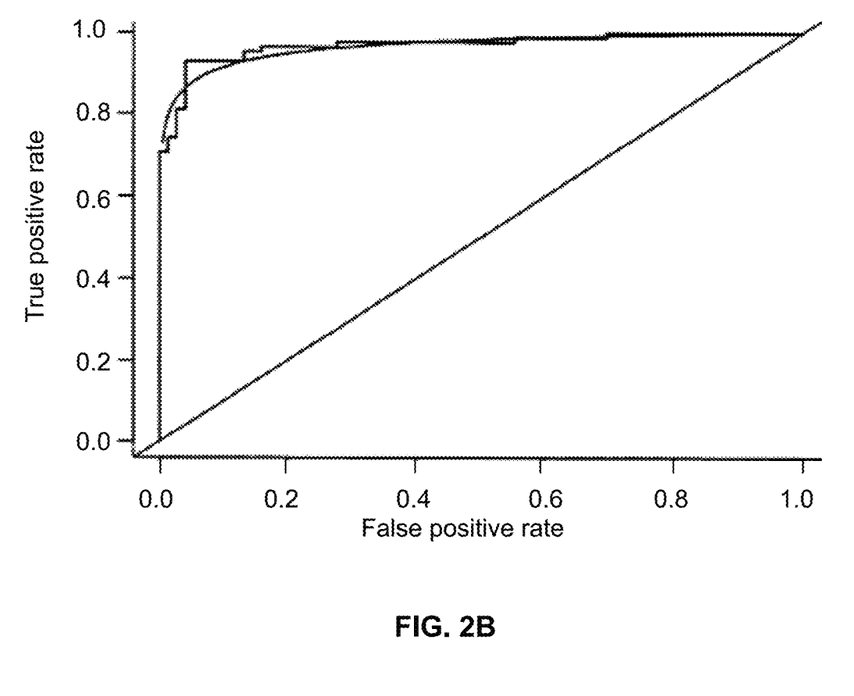

Incorporating patient's demographics, smoking and size of the pulmonary nodules with the two biomarkers, the logistic model is $Pr(y=1,cancer|U_3)=\exp(U_3)/1+\exp(U_3)$, and $U_3=-6.302+0.484\times\log_2(U6-486)+5.042\times CT+0.689\times\log_2 SP$ where SP is smoking-pack-years. The estimated AUC is 0.97. With the cut-off point Pr(y=1)=0.298, the sensitivity and specificity are 0.929 and 0.961, respectively (FIG. 2B). After analysis of only two genes in sputum, given the age and smoking history, the smokers with Pr>0.298 could be diagnosed with lung cancer.

EXAMPLE 3

Sputum miRNAs can Discriminate Between NSCLC Lung Cancer Patients and Controls

Figure 3A:
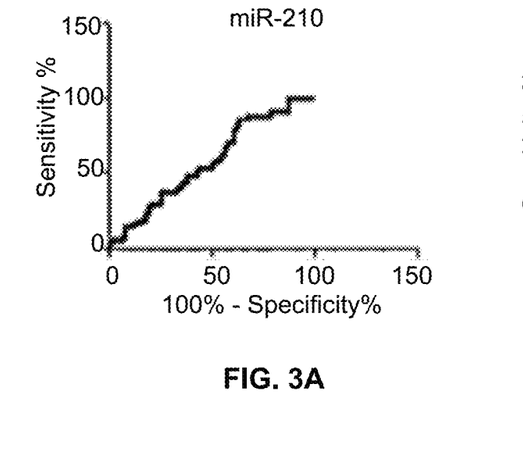
FIGS. 3A-3K are ROC curves of 11 miRNAs that differentially express in sputum between lung cancer patients and controls.
Figure 3B:
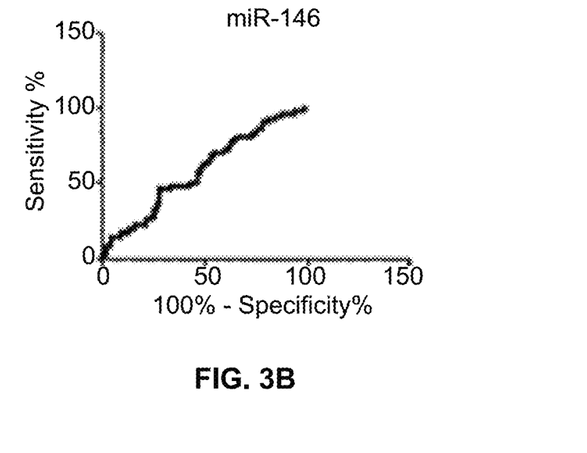
Figure 3C:
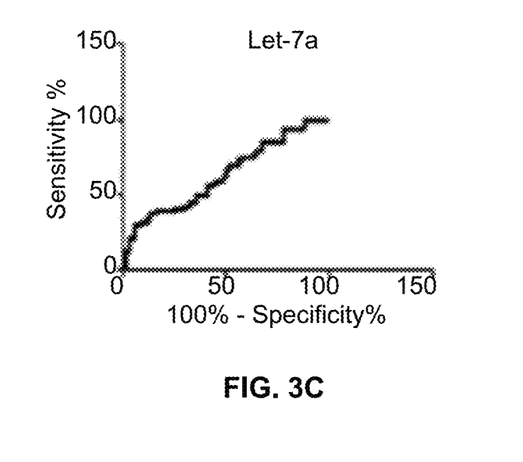
Figure 3D:
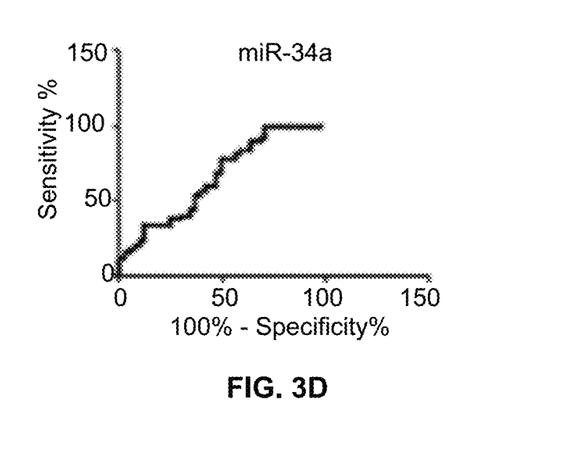
Figure 3E:
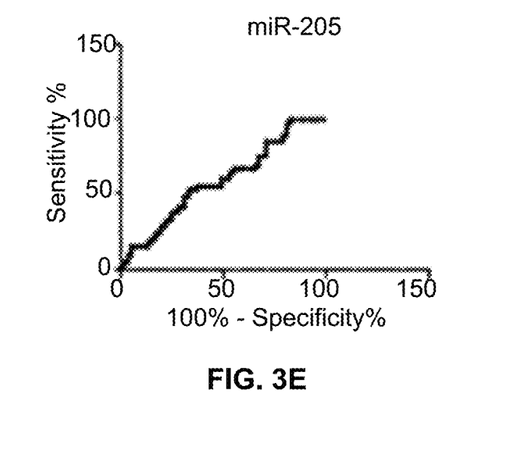
Figure 3F:
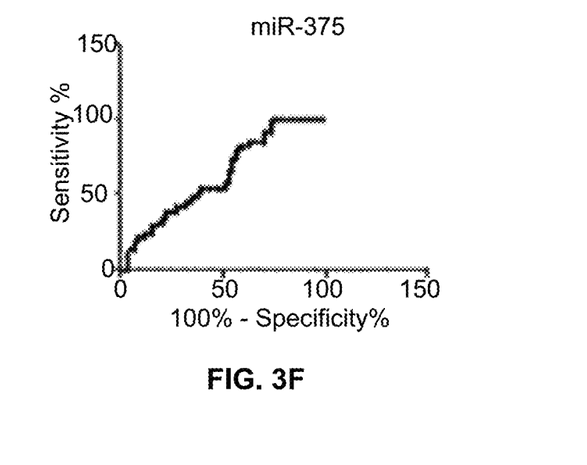
Figure 3G:
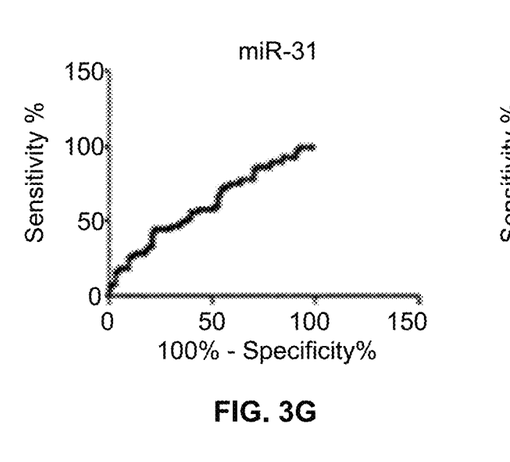
Figure 3H:
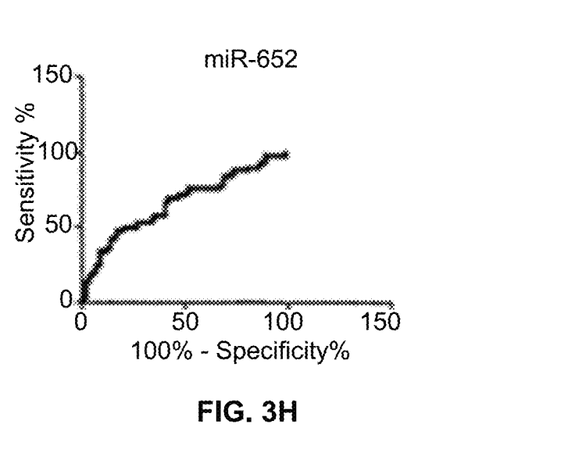
Figure 3I:
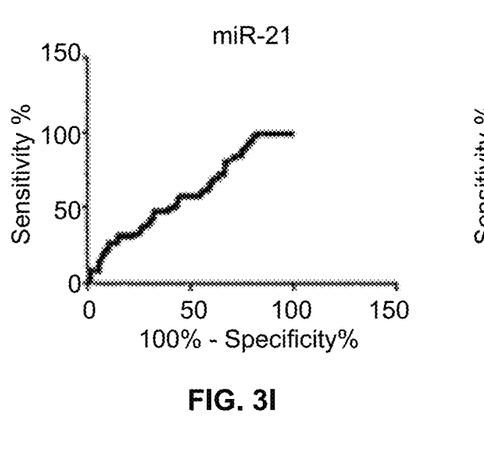
Figure 3J:
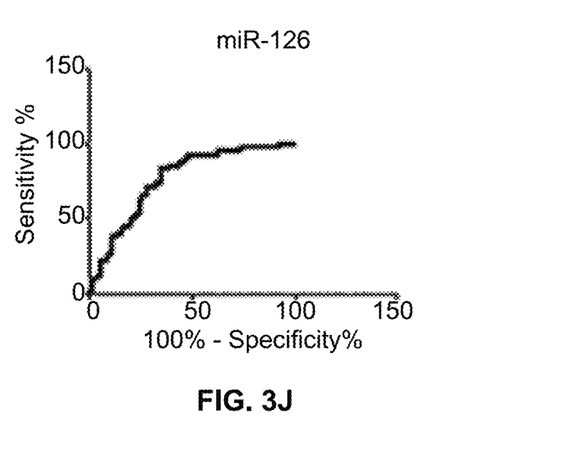
Figure 3K:
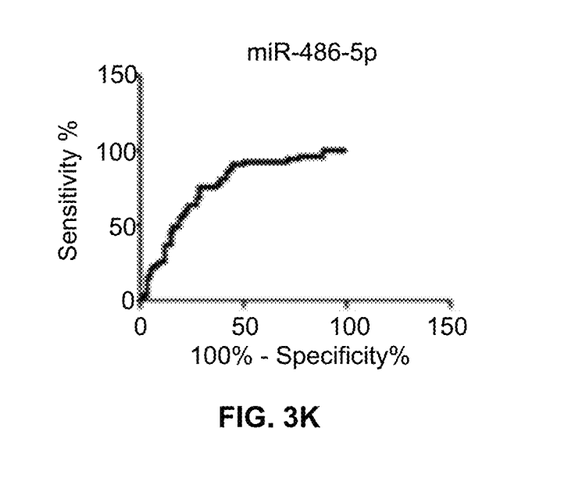

ROC curve analysis was applied to evaluate the capacity of using each of miR-210 (FIG. 3A), miR-146 (FIG. 3B), Let-7a (FIG. 3C), miR-34a (FIG. 3D), miR-205 (FIG. 3E), miR-375 (FIG. 3F), miR-31 (FIG. 3G), miR-652 (FIG. 3H), miR-21 (FIG. 3I), miR-126 (FIG. 3J) and miR-486-5p (FIG. 3K) for discriminating lung cancer patients from controls. The individual miRNAS exhibit AUC values of 0.609-0.786 in distinguishing non-small cell lung cancer (NSCLC) cancer cases from controls. Table 3 identifies seven of these miRNAs whose expressions in sputum are associated with a stage of NSCLC.

TABLE 3

Genes in sputum associated with NSCLC

| miRNAs | Pearson's coefficient | p-value |
|---|---|---|
| miR-146a | 0.346 | 0.0103 |
| miR-652 | 0.408 | 0.0080 |
| miR-34a | 0.461 | 0.0018 |
| miR-31 | 0.371 | 0.0067 |
| Let-7a | 0.296 | 0.0314 |
| miR-205 | 0.301 | 0.0231 |
| miR-210 | 0.270 | 0.0385 |

EXAMPLE 4

The Characteristics of Subjects and Sputum Samples 844 individuals were recruited from January 2006 to December 2011, from whom sputum samples were collected using protocols, including spontaneously coughing and inducing sputum by the Lung Flute (19, 28). Among the 844 participants, 160 (18.9%) could not spontaneously expectorate sputum, and thus underwent sputum induction by using the Lung Flute (28, 37). All the 160 individuals were able to produce sputum using the Lung Flute. Furthermore, consistent with previous findings (37), sputum collected by the Lung Flute displayed comparable features as spontaneously expectorated sputum regarding sputum volume, cell number, and percentages of cell populations. Therefore, all the sputum samples were appropriate for the molecular analysis in this study.

Of the 844 individuals, 316 were NSCLC patients and 528 were cancer-free smokers. Of the 316 lung cancer patients, 103 were diagnosed with stage I NSCLC, 105 with stage II and 108 with stage III-IV stage NSCLC. Because the objective was to evaluate the individual and combined applications of the two different types of ncRNAs in sputum for the early detection of lung cancer, sputum samples of the 103 stage I NSCLC patients were tested for the molecular analysis. Furthermore, from the 528 cancer-free subjects, 117 individuals were selected randomly as control cases.

The 103 stage I NSCLC cases and 117 cancer-free smokers were further randomly split into a training set and an internal testing set using a validated random number generator. The training set comprised 46 NSCLC patients and 55 cancer-free subjects (Table 4). The 103 stage I NSCLC cases had a median age of 65.3 years. Twenty-eight (60.9%) were men and 30 (65.2%) were white Americans. Twenty-five (54.3%) lung cancer cases were categorized to have adenocarcinoma (AC), and 21 (45.7%) have squamous cell carcinoma (SCC). All the NSCLC cases were smokers with a median of 44 pack-years of smoking. The 55 cancer-free smokers had a median of 43 pack-years of smoking, of whom, 33 (60.0%) were men and 36 (65.5%) were white Americans. The cancer-free subjects had granulomatous inflammation (n=29), nonspecific inflammatory changes (n=15), or lung infections (n=11).

TABLE 4

Characteristics of lung cancer patients and cancer-free smokers of a training set

| | NSCLC cases (n = 46) | Controls (n = 55) | P-value |
|---|---|---|---|
| Age | 65.28 (SD 11.27) | 67.65 (SD 11.34) | 0.35 |
| Sex | | | 0.38 |
| Female | 18 | 22 | |
| Male | 28 | 33 | |
| Race | | | 0.08 |
| white | 30 | 36 | |
| African American | 16 | 19 | |
| Pack-years | 44.79 | 43.45 | |
| | (Range, 5-172) | (Range, 5-109) | |
| FEV1/FVC | 0.45-079 | 0.43-0.80 | 0.38 |
| Nodule size (cm) | 4.79 | 1.29 | 0.10 |
| | (Range, 95.25) | (Range, 56.76) | |
| Stage, all are stage 1 | | | <0.01 |
| Histological type | | | |
| Adenocarcinoma | 25 | | |
| Squamous cell carcinoma | 21 | | |

The testing cohort included 57 stage I NSCLC cases and 62 cancer-free individuals (Table 5). The lung cancer cases had a median age of 64.3 years. Thirty-five (61.4%) were men and 37 (64.9%) were white Americans. Thirty-one (54.4%) lung cancer cases had AC, and 26 (45.6%) had SCC. The lung cancer cases had a median of 43.9 pack-years of smoking. The 62 cancer-free controls had a median age of 66.7 years and a median of 42.6 pack-years of smoking. Thirty-nine (62.9%) were men and 40 (64.5%) were white Americans. The cancer-free individuals had granulomatous inflammation (n=32), nonspecific inflammatory changes (n=16), or lung infections (n=14). No significant difference of the age, race, FEV1/FVC, and smoking status was found between the lung cancer cases and control subjects (All p>0.05), except size of PNs (Tables 4-5).

TABLE 5

Characteristics of lung cancer patients and cancer-free smokers of a testing set

| | NSCLC cases (n = 57) | Controls (n = 62) | P-value |
|---|---|---|---|
| Age | 64.26 (SD 12.37) | 66.69 (SD 10.88) | 0.36 |
| Sex | | | 0.39 |
| Female | 22 | 23 | |
| Male | 35 | 39 | |
| Race | | | 0.09 |
| white | 37 | 40 | |
| African American | 20 | 22 | |
| Pack-years | 43.89 | 42.64 | |
| | (Range, 5-170) | (Range, 5-112) | |
| FEV1/FVC | 0.46-078 | 0.44-0.79 | 0.39 |
| Nodule size (cm) | 4.89 | 1.54 | 0.09 |
| | (Range, 96.22) | (Range, 54.89) | |
| Stage, all are stage 1 | | | <0.01 |
| Histological type | | | |
| Adenocarcinoma | 31 | | |
| Squamous cell carcinoma | 26 | | |

EXAMPLE 5

Combined Analysis of the miRNAs and snoRNAs in Sputum has a Synergistic Effect for Lung Cancer Early Detection The three miRNAs and two snoRNAs had ≤30 Ct values in all sputum samples, and therefore were reliably detectable in the specimens by using a qTR-PCR assay. No product was synthesized in the negative control samples. As shown in Table 6, each of the five ncRNAs displayed a significantly higher level in sputum samples of the stage I NSCLC patients compared with the control subjects (all P<0.05). Furthermore, the individual ncRNAs exhibited AUC values of 0.78-0.84 in differentiating lung cancer cases from control subjects.

TABLE 6

Expression levels of the sputum ncRNAs in stage 1 NSCLC patients versus cancer free controls

| ncRNAs | Mean of level in NSCLC (SEM) | Mean of level in controls (SEM) | P-value | AUC 95% CI | Sensitivity | Specificity |
|---|---|---|---|---|---|---|
| miR-21 | 56.25 (6.89) | 7.64 (1.38) | <0.0001 | 0.81 (0.69 to 0.89) | 78.26 | 70.91 |
| miR-31 | 2.84 (0.38( | 0.46 (0.05) | <0.0001 | 0.78 (0.73 to 0.82) | 60.87 | 83.64 |
| miR-210 | 69.26 (6.58) | 5.89 (0.45) | <0.0001 | 0.84 (0.79 to 0.89) | 73.91 | 85.45 |
| snoRD66 | 0.72 (0.20) | 0.03 (0.06) | <0.0001 | 0.82 (0.76 to 0.90) | 63.04 | 80.00 |
| snoRD78 | 0.57 (0.11) | 0.22 (0.04) | <0.0001 | 0.81 (0.74 to 091) | 69.57 | 78.18 |
| Combine | | | <0.0001 | 0.94 (0.92 to 0.96) | 89.13 | 89.09 |

SEM, the standard error of the mean;
CI, confidence interval

Figure 4A:
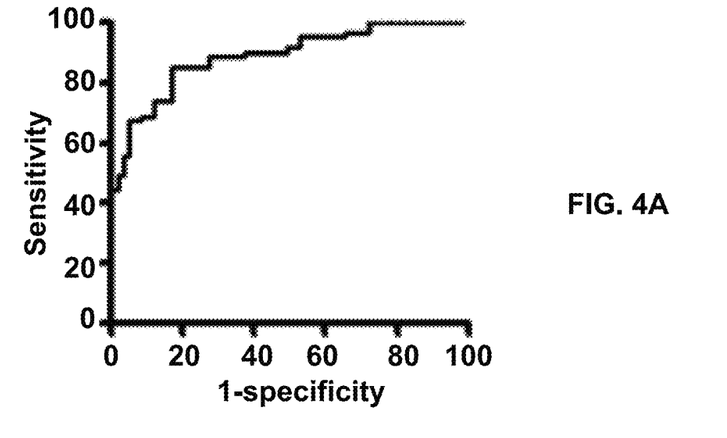
FIG. 4A is a ROC curve of a panel of three sputum miRNA biomarkers (miRs-21, 31, and 210) with an AUC of 0.90 for differentiating NSCLC patients from the cancer-free subjects in terms of sensitivity and specificity.
Figure 4B:
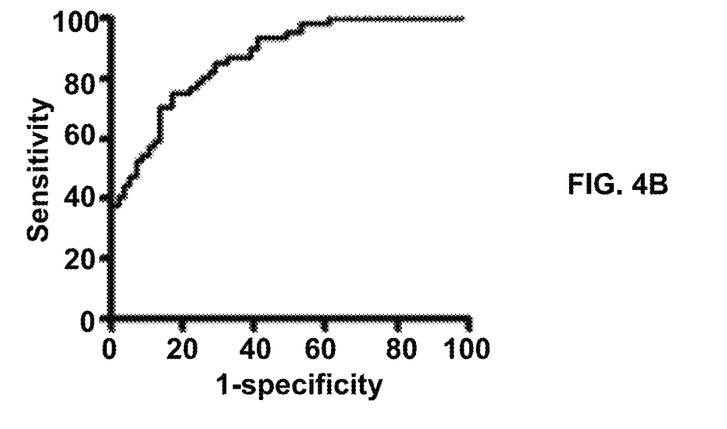
FIG. 4B is a panel of two snoRNA sputum biomarkers (snoRDs-66 and 78) that creates an AUC of 0.86 for distinguishing NSCLC patients from the cancer-free subjects.
Figure 4C:
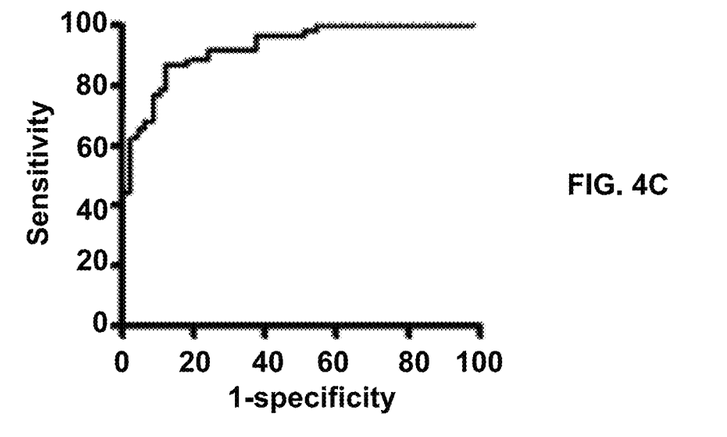
FIG. 4C is a combined study of the three miRNAs and two snoRNAs in sputum which yields a 0.90 AUC, which is significantly higher than that of any single type of ncRNAs used alone (P<0.05) for lung cancer detection.

Logistic regression models with constrained parameters as in LASSO and AUCs were used to determine performance of different patterns of combining the miRNA and snoRNA biomarkers for lung cancer detection. The panel of three miRNA and panel of two snoRNA had an AUC of 0.90 and 0.86, respectively. Interestingly, combined use of the five ncRNAs produced 0.94 AUC (FIG. 4C), which were statistically higher than that of the panel of three miRNA (0.90) (FIG. 4A) or the panel of two snoRNA (0.86) (FIG. 4B) used alone (p<0.05). Furthermore, the use of the five genes together generated 89.13% sensitivity, 89.09% specificity, and 89.10% accuracy. The panel of the three miRNA yielded 82.61% sensitivity, 85.45% specificity, and 84.16% accuracy. The panel of the two snoRNA produced 73.91% sensitivity, 83.64% specificity, and 79.21% accuracy.

Figure 5:
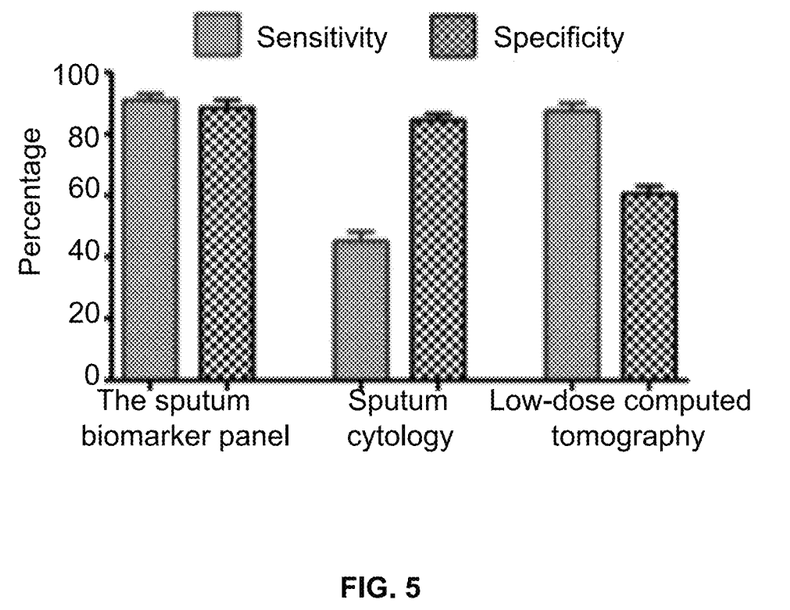
FIG. 5 compares the sensitivity and specificity of a combined panel of sputum biomarkers miR-21, miR-31, miR-210, snoRD66, and snoRD78 to the sensitivity and specificity of sputum cytology and low-dose computed tomography in lung cancer screening.

Therefore, combined analysis of the five ncRNAs had higher sensitivity, specificity, and accuracy compared with the individual panels of the three miRNA and the two snoRNA (All P<0.05). In addition, Pearson correlation analysis indicated that the estimated correlations among expression levels of the five ncRNAs were low (All P>0.05), implying that the diagnostic vales of the genes were complementary to each other. Moreover, sputum cytology had 45.65% sensitivity and 90.91% specificity. Therefore, combined application of the five sputum biomarkers had a higher sensitivity (P=0.01) and a similar specificity compared with sputum cytology (P=0.39). The expression level of the three miRNAs and two snoRNAs was associated with smoking history and size of PN of participants (All P<0.05). The expression level of sputum miR-21 was more closely related with AC (P<0.05), whereas miR-210 was associated with SCC (P<0.05). However, overall, the panel of the five ncRNA biomarkers didn't exhibit special association with a histological type of the NSCLC cases, and the age, gender, ethnicity, and FEV1/FVC of the participants (All P>0.05). Validating the Synergistic Effect of Combined Application of the Five Sputum ncRNA Biomarkers for Lung Cancer Detection The five sputum ncRNA biomarkers were validated in a testing cohort (Table 5) in a blinded fashion using the optimal thresholds established in the above training set. In FIG. 5 the panel of the five sputum ncRNA biomarkers had 89.47% sensitivity, 88.71% specificity, and 88.89% accuracy for lung cancer detection. Furthermore, sputum cytology showed 47.37% sensitivity and 90.32% specificity. The five sputum ncRNA biomarkers used in combination displayed a higher sensitivity (P=0.01) and a similar specificity (P=0.45) than did sputum cytology or low-dose computed tomography. Therefore, the results created from the validation study in a different set of cases and controls confirms use of the five sputum ncRNAs as a sputum biomarker panel for the early detection of NSCLC.

The following references are cited herein.
1. Cancer Facts & Figures 2012. American Cancer Society (ACS). Journal of Consumer Health on the Internet 2012; 16(3):366-367, 2012.
2. Aberle et al. N Engl J Med, 365(5):395-409, 2011.
3. Patz et al. JAMA Intern Med, 174(2):269-74, 2014.
4. Saccomanno et al. Acta Cytol, 9(6):413-23, 1965.
5. Mattick J S and Makunin I V. Hum Mol Genet, 15 Spec No 1:R17-29, 2006.
6. Esteller M. Nat Rev Genet, 12(12):861-74, 2011.
7. Deng G and Sui G. Int J Mol Sci, 14(9):18319-49, 2013.
8. Mei et al. Cancer Lett, 336(1):46-52, 2013.
9. Mannoor et al. Biochim Biophys Acta, 1826(1):121-8, 2012.
10. Mannoor et al. Mol Cancer, 13:104, 2014.
11. Mei et al. Oncogene, 31(22):2794-804, 2012.
12. Liao et al. Mol Cancer, 9:198, 2010.
13. Dong et al. Hum Mol Genet, 17(7):1031-42, 2008.
14. Su et al. Oncogene, 33(11):1348-58, 2014.
15. Williams et al. Nat Rev Cancer, 12(2):84-8, 2012.
16. Xie et al. Lung Cancer 2010; 67(2):170-6, 2010.
17. Su et al. Oncotarget 2015.
18. Yu et al. Int J Cancer, 127(12):2870-8, 2010.
19. Xing et al. Clin Cancer Res, 21(2):484-9, 2015.
20. Shen et al. J Thorac Oncol, 9(1):33-40, 2014.
21. MacMahon et al. Radiology, 237(2):395-400, 2005.
22. Henschke et al. Lung Cancer, 35(2):143-8, 2002.
23. Henschke et al. Radiology, 231(1):164-68, 2004.
24. Romeo et al. J Mol Diagn, 5(2):103-12, 2003.
25. Varella-Garcia et al. Cancer Detect Prev, 28(4):244-51, 2004.
26. Yu et al. Clin Lung Cancer 2014.
27. Li et al. J Cancer Res Clin Oncol, 140(1):145-50, 2014.
28. Anjuman et al. Clin Transl Med, 2(1):15, 2013.
29. Jiang et al. Cancer Prev Res (Phila), 3(12):1571-78, 2010.
30. Xing et al. Mod Pathol, 23(8):1157-64, 2010.
31. Jiang et al. Lung Cancer, 66(1):58-63, 2009.
32. Katz et al. Mod Pathol, 21(8):950-60, 2008.
33. Qiu et al. Cancer, 114(4):275-83, 2008.
34. Li et al. Clin Cancer Res, 13(2 Pt 1):482-7, 2007.
35. Machida et al. Cancer Res, 66(12):6210-18, 2006.
36. Belinsky et al t. Cancer Res, 66(6):3338-44, 2006.
37. Su et al. Biomark Insights, 10:55-61, 2015.
38. Kadara H and Wistuba, II. Proc Am Thorac Soc, 9(2): 38-42, 2012.
39. Brody J S and Spira A. Proc Am Thorac Soc, 3(6):535-37, 2006.
40. Belinsky et al. Cancer Res; 62(8):2370-77, 2002.
41. Hubers et al. Br J Cancer, 109(3):530-37, 2013.
42. Croce C M and Calin G A. Cell, 122(1):6-7, 2005.
43. Tang et al. Cancer Res, 65(17):7568-72, 2005.
44. Solis et al. Cancer, 118(11):2889-99, 2012.
45. Xu et al. PLoS One, 9(8):e103698, 2014.
46. Zhu et al. J Biol Chem, 282(19):14328-36, 2007.
47. Pezzolesi et al. Am J Hum Genet, 82(5):1141-9, 2008.
48. Valastyan S and Weinberg R A. Cell Cycle 2010; 9(11):2124-9, 2010.
49. Hong et al. Expert Opin Ther Targets 2013; 17(1):21-8, 2013.
50. McCormick et al. Curr Top Microbiol Immunol 2010; 345:47-70, 2010.
51. Gee et al. Cancer, 116(9):2148-58, 2010.
52. Camps et al. Clin Cancer Res, 14(5):1340-8, 2008.
53. Scapoli et al. Int J Immunopathol Pharmacol, 23(4): 1229-34, 2010.
54. Hong et al. Gene, 507(2):135-8, 2012.
55. Chang et al. J Vet Sci 2013; 14(1):69-76, 2013.
56. Lawrie et al. Br J Haematol, 141(5):672-5, 2008.
57. Papaconstantinou et al. Pancreas, 42(1):67-71, 2013.

What is claimed is:

1. A method for diagnosing and treating a non-small cell lung cancer in a human subject, comprising:
   a) obtaining a sputum sample from a human subject having a history of smoking;
   b) obtaining a control sputum sample from a cancer free control human subject having a history of smoking;
   c) measuring an expression level of each of MIR486-1 and MIR126 genes in the sputum sample and in the control sputum sample;
   d) applying a logistic regression model:

$Pr(y=1, \text{cancer}|U_1) = \exp(U_1)/1 + \exp(U_1)$, where, $U_1 = -0.302 + 0.175 \times \log_2(\text{MIR486-1}) + 0.336 \times \log_2(\text{MIR-126})$;

e) diagnosing non-small cell lung cancer in the human subject when the Pr (y=1) value is greater than 0.298; and f) administering a chemotherapeutic drug to the human subject diagnosed with non-small cell lung cancer.

2. The method of claim 1, wherein step d) further comprises adding values representative of pack-years of smoking for the human subject and for the human control subject to the logistic regression model.

3. The method of claim 1, wherein step d) further comprises adding values representative of a size of pulmonary nodules in the human subject and in the human control subject to the logistic regression model.

4. The method of claim 1, further comprising in the human subject diagnosed with non-small cell lung cancer:

repeating steps a) to d) at intervals during and after administering the chemotherapeutic drug for the non-small cell lung cancer; and comparing the Pr (y=1) value calculated at each interval with the initial Pr (y=1) value; wherein a comparison at each interval is an indicator of a therapeutic effectiveness of the chemotherapy drug.

5. A non-invasive method for early detection and treatment of a non-small cell lung cancer in a human subject, comprising:

a) obtaining a sputum sample from a human subject with a history of smoking and pulmonary nodules;

b) obtaining a control sputum sample from a cancer free control human subject with a history of smoking and pulmonary nodules;

c) measuring expression levels of MIR486-1 and MIR126 genes in the sputum sample and in the control sputum sample;

d) applying a logistic regression model:

$Pr(y=1, cancer | U_3) = \exp(U_3)/1 + \exp(U_3)$, where, $U_3 = -6.302 + 0.484 \times \log_2(MIR486\text{-}1) + 5.042 \times CT + \log_2 SP$ (smoking-pack-years);

e) diagnosing the non-small cell lung cancer in the human subject when the Pr (y=1) value is greater than 0.298; and f) administering a chemotherapeutic drug to the human subject diagnosed with non-small cell lung cancer.

* * * * *